(12) United States Patent
Diebold et al.

(10) Patent No.: US 11,147,485 B2
(45) Date of Patent: Oct. 19, 2021

(54) BODY FLUID EXTRACTION DEVICE

(71) Applicant: Midge Medical GmbH, Berlin (DE)

(72) Inventors: Michael Diebold, Berlin (DE); Markus Riester, Wiesbaden (DE); Jorn Bungartz, Chorin (DE)

(73) Assignee: MIDGE MEDICAL GMBH

( * ) Notice: Subject to any disclaimer, the term of this patent is extended or adjusted under 35 U.S.C. 154(b) by 316 days.

(21) Appl. No.: 16/098,506

(22) PCT Filed: May 3, 2017

(86) PCT No.: PCT/EP2017/060585
§ 371 (c)(1),
(2) Date: Nov. 2, 2018

(87) PCT Pub. No.: WO2017/191221
PCT Pub. Date: Nov. 9, 2017

(65) Prior Publication Data
US 2019/0142318 A1    May 16, 2019

(30) Foreign Application Priority Data
May 4, 2016    (DE) ..................... 10 2016 207 815.1

(51) Int. Cl.
*A61B 5/157* (2006.01)
*A61B 5/15* (2006.01)
(Continued)

(52) U.S. Cl.
CPC ............ *A61B 5/157* (2013.01); *A61B 5/1513* (2013.01); *A61B 5/150022* (2013.01);
(Continued)

(58) Field of Classification Search
CPC .............. A61B 5/157; A61B 5/150916; A61B 5/150022; A61B 5/150137;
(Continued)

(56) References Cited

U.S. PATENT DOCUMENTS

| 5,402,798 A | 4/1995 | Swierczek et al. |
| 6,340,354 B1 | 1/2002 | Rambin |
| (Continued) | | |

FOREIGN PATENT DOCUMENTS

| EP | 1 266 608 A2 | 12/2002 |
| WO | 2012/125424 A2 | 9/2012 |
| (Continued) | | |

OTHER PUBLICATIONS

Li, et al.; "A Minimally Invasive Blood-Extraction System: Elastic Self-Recovery Actuator Integrated with an Ultrahigh-Aspect-Ratio Microneedle"; Wiley Online Library; 2012; pp. 4583-4586.
(Continued)

*Primary Examiner* — Sean P Dougherty
*Assistant Examiner* — Alexander H Connor
(74) *Attorney, Agent, or Firm* — Ware, Fressola, Maguire & Barber LLP

(57) ABSTRACT

A device for extracting a body fluid and testing a predetermined analyte or property of the fluid is provided. The device comprises a hollow needle having a channel linking a base end and a tip, a collection chamber having an input end in fluid communication with the channel, a testing chamber, a solution chamber and a flow control. The collection chamber comprises a capillary wick configured to transport at least a fraction of the body fluid away from the input end. The testing chamber comprises a testing unit including a reacting material configured to react to a predetermined analyte or property of the fluid and the solution chamber comprises a buffer solution. A flow control is also provided for a transfer of the buffer solution from the solution chamber to the collection chamber and a transfer of the body fluid from the collection chamber to the testing chamber.

23 Claims, 15 Drawing Sheets

(51) Int. Cl.
*A61B 5/151* (2006.01)
*A61B 5/00* (2006.01)

(52) U.S. Cl.
CPC ...... *A61B 5/15105* (2013.01); *A61B 5/15117* (2013.01); *A61B 5/150137* (2013.01); *A61B 5/15144* (2013.01); *A61B 5/150221* (2013.01); *A61B 5/150251* (2013.01); *A61B 5/150389* (2013.01); *A61B 5/150755* (2013.01); *A61B 5/150916* (2013.01); *A61B 5/150969* (2013.01); *A61B 5/150984* (2013.01); *A61B 5/6833* (2013.01)

(58) Field of Classification Search
CPC ........ A61B 5/150221; A61B 5/150251; A61B 5/150389; A61B 5/15144; A61B 5/150969; A61B 5/150984; A61B 5/15105; A61B 5/15117; A61B 5/1513; A61B 5/6833; A61B 5/150755
See application file for complete search history.

(56) References Cited

U.S. PATENT DOCUMENTS

| | | | |
|---|---|---|---|
| 8,821,413 | B2 | 9/2014 | Effenhauser et al. |
| 2003/0135161 | A1 | 7/2003 | Fleming et al. |
| 2007/0078358 | A1 | 4/2007 | Escutia et al. |
| 2008/0300508 | A1* | 12/2008 | Tomer .............. A61B 5/150412 600/583 |
| 2011/0009847 | A1 | 1/2011 | Levinson et al. |
| 2011/0172510 | A1 | 7/2011 | Chickering, III et al. |
| 2012/0123297 | A1 | 5/2012 | Brancazio |
| 2012/0277697 | A1 | 11/2012 | Haghgooie et al. |
| 2013/0096400 | A1* | 4/2013 | Dahl ........................ A61B 5/15 600/317 |
| 2014/0323837 | A1 | 10/2014 | Hirshberg |
| 2015/0057510 | A1* | 2/2015 | Levinson ......... A61B 5/150221 600/309 |
| 2015/0202418 | A1* | 7/2015 | Simon .................... A61F 13/53 604/319 |

FOREIGN PATENT DOCUMENTS

| | | |
|---|---|---|
| WO | 2012/149143 A1 | 11/2012 |
| WO | 2014/016579 A1 | 1/2014 |
| WO | 2014/172243 A1 | 10/2014 |
| WO | 2015/048777 A1 | 4/2015 |
| WO | WO-2016148646 A1 * | 9/2016 ....... A61B 5/150358 |

OTHER PUBLICATIONS

Wang, et al; "Development of Wearable Semi-invasive Blood Sampling Devices for Continuous Glucose Monitoring: A Survey"; Scientific Research, Engineering; 2013; pp. 42-46.

Gattiker, et al; "Electronic Mosquito: designing a semi-invasive Microsystem for blood sampling, analysis and drug delivery applications"; Microsyst Technol; Sep. 21, 2005; pp. 44-51.

Li, et al; "A self-powered one-touch blood extraction system: a novel polymer-capped hollow microneedle integrated with a pre-vacuum actuator"; The Royal Society of Chemistroy 2015; pp. 382-390.

Matsuura, et al; "Development of a blood extraction device for a miniature SMBG system"; BioMEMS and Nanotechnology III; vol. 2799; 2007; pp. 67990N-1 through 67990N-11.

\* cited by examiner

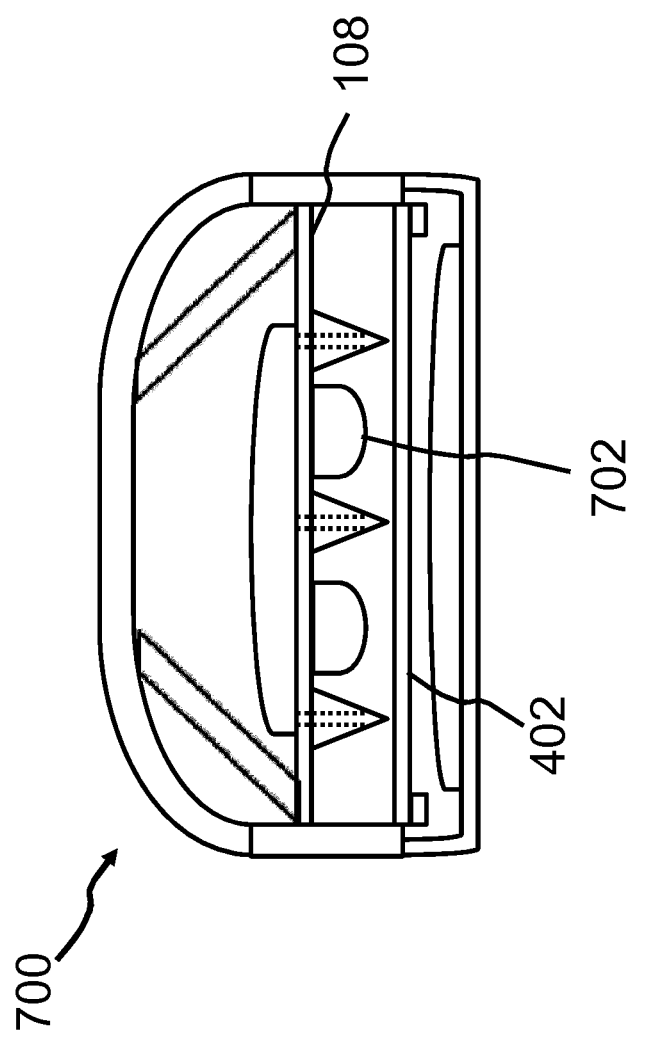

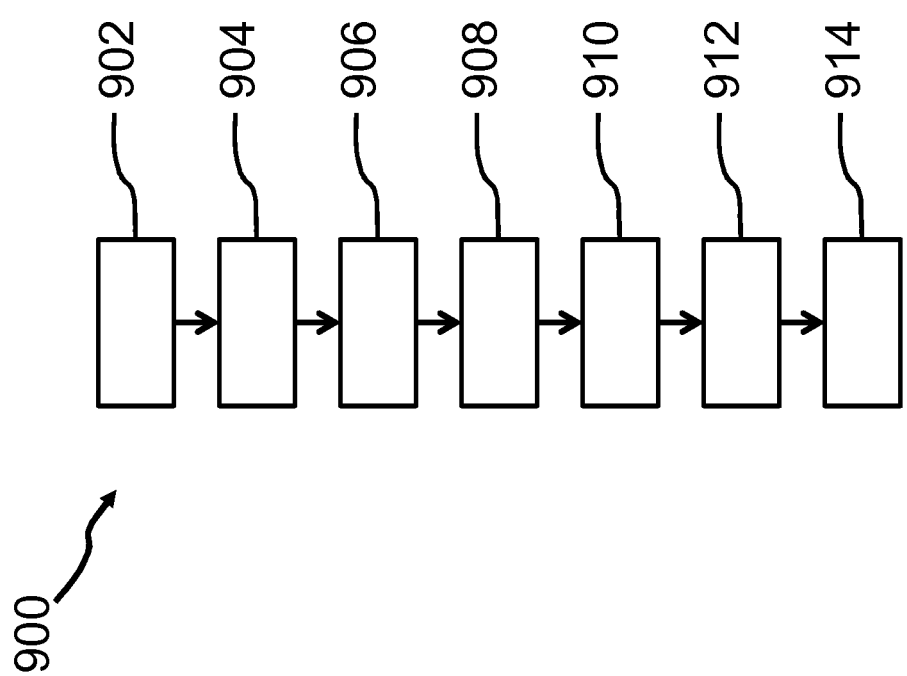

BODY FLUID EXTRACTION DEVICE

CROSS REFERENCE TO RELATED APPLICATIONS

This application is the U.S. National Stage of International Application Number PCT/EP2017/060585 filed on May 3, 2017, which application claims priority under 35 USC § 119 to German Patent Application No. 10 2016 207815.1 filed on May 4, 2016. Both applications are hereby incorporated by reference in their entirety.

FIELD OF THE INVENTION

The present invention relates to a body fluid extraction device for extracting a body fluid and for testing at least one predetermined analyte or property of the body fluid, to another body fluid extraction device for extracting body fluids through a skin surface and to a method for operating a body fluid extraction device.

BACKGROUND OF THE INVENTION

U.S. Pat. No. 8,821,413 B2 provides a system for withdrawing small amounts of body fluid from an animal or human. The system includes a holder and a disposable lancing unit attached to the holder. The lancing unit also includes an open capillary channel for piercing the skin and transporting the body fluid to a detection area.

Cheng Guo Li et al (Lab Chip, 2015, 15, 382-390, DOI: 10.1039/c14c00937a) present a self-powered one touch blood extraction system comprising a novel polymer capped hollow microneedle integrated with a pre-vacuum actuator. The entire system is made of low-cost and disposable materials to achieve easy operation with a miniature structure and to meet the challenging requirements for single use application in a point of care system without the use of any external power equipment.

SUMMARY OF THE INVENTION

It would be beneficial to provide a body fluid extraction device that requires less body fluid than known devices to perform a test of a predetermined analyte or property of the body fluid. Body fluids, also referred to as bodily fluids, are liquids that originate from inside bodies of living beings. A non-exhaustive list of body fluids include, but is not limited to, blood, blood serum, lymph, amniotic fluid, aqueous and vitreous humor, synovial fluid, cerebrospinal fluid, pericardial fluid, pleural fluid, peritoneal fluid, etc.

According to a first aspect of the present invention, a body fluid extraction device for extracting a body fluid and for testing at least one predetermined analyte or property of the body fluid is presented. The body fluid extraction device comprises at least one hollow needle having a base end and a tip and a channel linking the base end and the tip in fluid communication. It also comprises a collection chamber having an input end in fluid communication with the channel. The collection chamber comprises a capillary wick configured to transport at least a fraction of the body fluid away from the input end. The body fluid extraction device also comprises a testing chamber comprising at least one testing unit that includes a respective reacting material configured to react in a predetermined manner to a predetermined analyte or property of the body fluid, a solution chamber, comprising a buffer solution and flow control means configured to control, in a first step, a first transfer of the buffer solution from the solution chamber to the collection chamber, and in a second step a second transfer of the body fluid and the buffer solution from the collection chamber to the testing chamber.

The tip of the hollow needle is configured to be inserted into a human being to extract the body fluid. The extracted body fluid travels inside the channel linking the tip with the base end to the input end of the collection chamber, which is in fluid communication with the channel. The collection chamber comprises a capillary wick that is configured to transport by capillary action, at least a fraction of the body fluid in a direction away from the input end, i.e. the position where the body fluid enters the collection chamber. The capillary wick transports the body fluid to a testing chamber. The testing chamber comprises one or more testing units. Testing of the body fluid in the testing units is performed using a reacting material that is configured to react in a predetermined manner to a predetermined analyte or property of the body fluid.

In order to favor the transport of the body fluid from the collection chamber to the testing chamber, the extraction device further comprises a solution chamber that houses a buffer solution and flow control means. In a preferred embodiment the buffer solution is a liquid solution that simply dilutes the body fluid but does not further interfere with the testing of the body fluid in the testing chamber. In a first step the flow control means control a first transfer of the buffer solution from the solution chamber to the collection chamber. This increases the volume of fluid present in the collection chamber and enhances the capillary action which in turn increases a transport velocity of the fluid inside the collection chamber. The flow control means are further configured to control, in a second step, a second transfer of both, the body fluid and the buffer solution, from the collection chamber to the testing chamber.

The buffer solution that is originally comprised by the solution chamber is advantageously configured to enhance a transport velocity of the body fluid towards the testing chamber and also increase a total volume of solution that is to be transported to the testing chamber.

In the following, embodiments of the body fluid extraction device of the first aspect of the invention will be presented.

The analyte or analytes that the present invention is configured to test are, in different embodiments, a predetermined target chemical element, a target ion, target molecule or groups of molecules including organic and/or inorganic substances, target cells or groups of cells, etc. In other embodiments a property of the body fluid is tested. A non limiting example of a property of the bodily fluid that a particular embodiment of the first aspect of the invention is configured to test is a pH-value of the body fluid.

In some embodiments the buffer solution is transferred from the solution chamber to the collection chamber via the input end of the collection chamber. These embodiments are advantageously configured to enhance the transport of the body fluid away from the input end and thus prevent a loss of body fluid through the hollow needle due to backflow.

Minimizing sanitary risks is of major importance for body fluid extraction devices in general. Therefore parts of the device that are configured to be in contact with the subject from which the body fluid is to be extracted should be kept sterile before extraction of the body fluid. In some embodiments of the body fluid extraction device the hollow needle, the collection chamber and the solution chamber are arranged inside a sealed chamber.

This sealed chamber comprises in some embodiments a sealing membrane configured to maintain a sterile condition of the hollow needle, the collection chamber and the solution chamber. In these embodiments, the testing chamber is arranged outside the sealed chamber. The sealed chamber and the testing chamber are configured to be brought into fluid communication upon transferring the body fluid and the buffer solution from the collection chamber to the testing chamber. In some of these embodiments, the sealed chamber is configured to be pierced by the hollow needle prior to extraction of the body fluid. In other embodiments, the sealed chamber comprises a protective cover and a sealing membrane. The protective cover covers at least the hollow needle and can be removed before extraction of the body fluid. The sealing membrane separates the collection chamber and the testing chambers until they are brought in fluid communication during the second transfer of the body fluid and the buffer solution from the collection chamber to the testing chamber.

These embodiments are particularly beneficial since they decouple an extracting functionality from a testing functionality of the body fluid extraction device. Once the body fluid and the buffer solution are in the collection chamber the sealed chamber and the testing chamber are brought into fluid communication by the flow control means. In this manner, one of several different available testing chambers can be coupled with a single sealed chamber prior to use, thus reducing production costs of the body fluid extraction device.

The at least one testing unit comprises in some embodiments a lateral flow assay unit. The lateral flow assay units include a respective sample pad configured to adsorb the body fluid and the buffer solution after the second transfer and a testing capillary wick connected to the sample pad and wherein the reacting material is arranged on said testing capillary wick.

Lateral flow assays are known to the skilled person as assays intended to detect the presence or absence of a target analyte of the body fluid or a property of the body fluid. In lateral flow assays a liquid sample of the body fluid moves without the assistance of external forces (for example by capillary action) through various zones of the lateral flow assay unit. The liquid sample is applied on the sample pad and then migrates along the testing capillary wick into a detection zone comprising the reacting materials. In some particular embodiments, the testing unit further comprises a conjugate release pad which contains conjugated antibodies that are specific to the analyte that is to be tested. The reacting material comprises specific biological components such as antibodies or antigens, which are configured to react with the analyte bound to the respective conjugated antibody. Recognition of the particular analyte results in a predetermined reaction of the reacting material. In some embodiments the reacting material is arranged in the form of lines. Some embodiments comprise a plurality of lines of reacting material and can advantageously be used for semi-quantitative analysis.

In some of these embodiments the testing chamber comprises a plurality of testing units that have a respective reacting material configured to react in a predetermined respective manner to a predetermined respective analyte or property of the body fluid. These embodiments are advantageously configured to perform more than one test of a respective analyte of the body fluid, to determine more than one property of the body fluid, or any combination thereof. In some of these embodiments, the plurality of testing units are arranged to share a common sample pad. The respective testing capillary wicks extend radially from a common center formed by the common sample pad. In these embodiments, the second transfer of the body fluid and the buffer solution brings the body fluid and the buffer solution to the common sample pad. The body fluid and the buffer solution then migrate along the respective testing capillary wicks towards the respective reacting material.

The flow control means allow for a first transfer of the buffer solution from the solution chamber in a first step and for a second transfer of the body fluid and the buffer solution from the collection chamber to the testing chamber in a second step. The first set and the second step may take place sequentially or simultaneously.

In some embodiments of the body fluid extraction device, the testing solution chamber comprises a first pierceable wall section. In these embodiments, the flow control means comprises a first cannula configured to pierce the first pierceable wall section, and upon piercing the first pierceable wall section, to bring the solution chamber in fluid communication with the collection chamber. These embodiments provide a technologically simple implementation of the flow control means.

Other embodiments additionally or alternatively include a testing chamber that comprises a second pierceable wall section and wherein the flow control means comprises a second cannula configured to pierce the second pierceable wall section and, upon piercing the second pierceable wall section, to bring the collection chamber in fluid communication with the testing chamber.

In other embodiments the flow control means comprise a first fluid connection between the solution chamber and the collection chamber, the first fluid connection being controllable by a first valve in dependence on a predetermined first control signal. Additionally or alternatively other embodiments comprise a second fluid connection between the collection chamber and the testing chamber, the second fluid connection being controllable by a second valve in dependence on a predetermined second control signal.

In yet further embodiments, the flow control means comprise a combination of a controllable valve and a cannula, wherein the controllable valve and the cannula control the first transfer and second transfer respectively. In yet other embodiments comprising a combination of a controllable valve and a cannula, the controllable valve and the cannula control the second transfer and first transfer respectively, In order to enhance the capillary effect inside the linking channel of the hollow needle, some embodiments comprise a hollow needle that has an inner wall of the channel that is at least partially covered by a covering layer comprising a hydrophilic material.

Most body fluid samples are obtained using a painful hypodermic needle puncture. The application of microneedles and microactuators has allowed researchers to develop miniaturized fluid extraction systems.

Nevertheless and despite the miniaturization efforts leading to less painful experiences for those whose body fluids are extracted, some users who have to extract body fluids from their own bodies experiment needle phobia which is a defined medical condition that affects over 20% of the adult population to such an extent that it may even cause them to avoid needed medical care. It is therefore desirable to provide a body fluid extraction device where the insertion of the needle through the skin does not solely depend on the pressure applied by the user, so that even a user with needle phobia would be able to use the extraction device on him or herself.

It has also been recognized by the inventor, that the use of a snap dome tripper that induces a snap movement on a needle carrier to which at least one needle is attached can be advantageously used to decouple the application of a force to a body fluid extraction device from the actual piercing of the skin by the at least one needle. Therefore, and according to a second aspect of the present invention, a body fluid extraction device for extracting body fluids through a skin surface is provided. The extraction device comprises:

- at least one hollow needle having a base end and a tip and a channel linking the base end and the tip in fluid communication;
- a needle carrier to which the hollow needle is attached or integrated, the needle carrier comprising an outer side configured to face the skin surface upon operation of the extraction device and an inner side opposite to the outer side, wherein a length of the needle comprising the needle tip extends out of the outer side of the needle carrier;
- a support structure connected to the needle carrier and configured to allow a relative movement of the needle carrier relative to the support structure in a direction substantially perpendicular to the skin surface; and
- a snap dome tripper connected to the support structure, the snap dome tripper arranged and configured to induce a snap movement of the needle carrier relative to the support structure.

The extraction device of the second aspect of the present invention uses the snap dome tripper mechanism advantageously to overcome the user's psychological barrier of having to puncture his or her own skin surface to extract body fluids. It can however also be used by a user to extract body fluids from another subject. Therefore, in the frame of this invention, the user is defined as the person operating the extraction device, and the subject is defined as the person whose body fluids are subject to be extracted by the extraction device. It is therefore clear that the user and the subject may or may not be the same person. In the present invention, it is the snap dome tripper which, upon being operated by the user, induces a snap movement of the needle carrier relative to the support structure and towards the surface of the skin with the aim to puncture the skin surface and extract the body fluids. The role of the user is reduced to induce the snap movement and not to directly insert the needle into the skin. A snap movement is to be understood, in the frame of this invention, as a transition of the snap dome tripper from a stable state to another stable or metastable state. Examples of devices not related to this invention that show similar properties are hair clips which work by snapping the clip from a concave to a convex position (both states being in this case stable states) or a clicker or Knackfrosch, where one state is metastable, i.e. the clicker in the metastable state returns to the stable state after a predetermined time span that depends, among other things, on the material and the geometry of the device. The at least one hollow needle is advantageously configured to minimize the pain on the user while guaranteeing a sufficient volume of extracted fluid, and may comprise an array of hollow microneedles advantageously configured to favor the extraction of the body fluids by, for example but not limited to, capillary action or pressure gradient.

In the following, embodiments of the body fluid extraction device of the second aspect will be presented.

In some embodiments, the snap dome tripper comprises an arched or dome-shaped applicator configured to be deflected by exerting a predetermined activation force on the arched or dome-shaped applicator, activation force corresponding to or being higher than an amount of force required to push the hollow needle into the skin surface. In these embodiments, the user applies a predetermined activation force that corresponds to the force required to bring the needle in contact with the skin and to initiate the insertion. Once this force is applied by the user, the snap movement is induced, decoupling the further insertion of the needles from the amount of force exerted by the user. In cases where the user is also the subject, he is only required to apply the activation force on the arched or dome-shaped applicator and not to apply the whole necessary force to fully insert the needles into the skin surface.

In other embodiments of the second aspect of the invention, the extraction device comprises at least one collection unit configured to collect the body fluid, the collection unit being in fluid communication with the base end of the hollow needle at the inner side of the needle carrier. In these embodiments, the body fluid flows from the body into the collection unit via the hollow needle. The extraction is facilitated in some embodiments by capillary action and in other embodiments by the existence of a pressure gradient, where the needles and the collection unit are configured to be at a lower pressure than the atmospheric pressure. Some embodiments have a plurality of independent collection units. The body fluids collected in each of the collection unit can be thus used for different purposes such as, but not limited to, different body fluid tests.

In order to further facilitate the extraction of the body fluids, some embodiments have collection units comprising an absorbing material in fluid communication with the base end of the needle. The absorber material is thus configured to aid in the extraction of the body fluid by physical or chemical absorption occurring between the body fluid and the absorbing material. Once the body fluid has reached the absorbing material by any of the above mentioned methods (e.g. capillarity, pressure gradient, etc.), the absorbing properties of the absorbing material accelerate the extraction process. The absorber materials used have to be chosen in dependence with their interaction properties with the body fluid to be extracted. They are thus configured not to interfere with certain predetermined characteristics of the body fluids. The absorber material is in some embodiments arranged as a capillary wick configured to transport at least a fraction of the body fluid away from the base end of the hollow needle. In some embodiments, cellulosic or fiber based materials are used. In other embodiments superabsorbing polymers or hydrogels are used. It would be desirable to aid the user by facilitating a way to attach the extraction device on the skin surface and avoid a displacement of a position of the extraction device upon operation. Therefore, some embodiments comprise a protective membrane connected to the support structure and configured to cover the outer side of the needle carrier, and wherein at least a portion of the protective membrane comprises an adhesive layer configured to attach the extraction device to the skin surface. The adhesive layer thus enables the user to fix the extraction device on the subject's skin surface before extracting the body fluids. The needles, in their movement towards and into the skin surface, also penetrate the protective membrane. In some embodiments, the protective membrane marks out a volume of the extraction device having a lower pressure and which comprises at least the hollow needles and the collection unit, which are in fluid communication. This lower pressure is in some embodiments advantageously configured to aid in the extraction of the body fluids, as explained above. The protective membrane is, in some embodiments, advantageously configured to avoid a contamination of the needles with contaminants from outside of the device. The protective membrane is in some embodiments made of polypropylene. In other embodiments the protective membrane is made of polyamide. Other embodiments have protective membranes made of other materials such as, but not limited to, polyethylene. In other embodiments the protective membranes consist of multiple layers of polymeric material. In yet other embodiments, the membranes consist of multiple layers of polymeric and metallic materials. In some embodiments, the adhesive layer is located at a perimeter of a most outer section of the protection membrane. These embodiments are particularly advantageous, since the needle or needles do not penetrate the adhesive layer before entering the surface skin and thus widening the choice of adhesive materials. In these embodiments, only properties regarding the skin compatibility of the adhesive layer have to be considered, since with this configuration there is no risk of inserting part of the adhesive material together with the needle into the skin. In some embodiments, the adhesive layer covers the protective layer except at those positions where the needles penetrate the protective layer.

Since the extraction device is designed to extract body fluid and therefore to be in contact with the inner parts of a body, it is convenient that it is kept in sterile conditions at least prior to its use. Therefore, some embodiments of the second aspect of the present invention also include a detachable sealing layer connected to the support structure. The sealing layer has an internal side facing the outer side of the needle carrier and an external side opposite to the internal side. The sealing layer is configured to cover hermetically the protective membrane. The sealing layer is thus arranged to hermetically seal the extraction device, and to avoid the presence of external chemical or biological contaminants on the needle or the collection unit. In other embodiments, the sealing layer is also advantageously configured to maintain the low pressure conditions inside the extraction device until it is used.

Applying the extraction device on properly conditioned skin surface is also beneficial since it avoids further contamination of the body fluid or the insertion of contaminants into the skin upon application of the extraction device. In order to properly condition the skin surface, some embodiments of the extraction device of the first aspect of the invention comprise a skin conditioning layer comprising an antiseptic material, the skin conditioning layer being attached to the internal side of the sealing membrane layer. The user can thus, upon detaching the sealing layer, apply the skin conditioning layer on the surface skin so as to cleanse the skin surface where the extraction device will be applied using the antiseptic material In some embodiments the antiseptic material comprises alcohols, such as, but not limited to ethanol, 1-propanol, isopropanol or mixtures thereof. In other embodiments, quaternary ammonium compounds are used. In other embodiments iodine-based antiseptic materials are used. Other embodiments comprise other skin-compatible antiseptic materials. The skin conditioning layer can be also used after extracting the body fluids to rinse the skin surface where the extraction device has been applied Once the extraction device has been used and body fluids have been conveniently extracted, it is desired that the needles cannot be further used, minimizing therefore, for example, the risk of contaminating the extracted body fluid or the risk for disease transmission by an involuntary piercing of another subject's skin. In some embodiments, the extraction device comprises an expandable material located between the outer side of the needle carrier and the protective membrane which, once the hollow needle has penetrated the protective membrane, is configured to expand, within a predetermined expansion time span, from an initial volume amount to a final volume amount, the final volume amount being larger than the initial volume amount, and wherein the expandable material having the final volume amount is configured to cover the tip of the hollow needle. The expandable material may be a material, such as, but not limited to, a foam, that reacts to a pressure stimulus, expands to a final volume and hardens. Other expandable materials may be, but are not limited to 2-component epoxy, 1-component epoxy, polystyrene, polyester, polyurethanes, etc. The needles are then located inside that final volume so that they cannot be intentionally, unintentionally or accidentally used again. These embodiments thus increase the safety of the extraction device providing a mechanism that renders the needles unusable after the extraction device has been used.

In other embodiments of the extraction device of the second aspect of the present invention the needle carrier is attached to an application layer having a first stable state and a second stable state, the application layer being connected to the snap dome tripper, and wherein the snap dome tripper is further configured to:
  trigger a first change on the application layer, from the first stable state to the second stable state, upon an occurrence of the snap movement;
  trigger a second change on the application layer, from the second stable state to the first stable state after an extraction time span has lapsed; and
  wherein a transition from the first stable state to the second stable state is configured to exert the predetermined activation force corresponding at least to the force required to push the hollow needle into the skin surface; and
  the transition from the second stable state to the first stable state is configured to facilitate an extraction of the hollow needle from the skin surface.

In these embodiments the application layer is a bistable material and the system is said to be "over center", that is, pressure is applied on the application layer, by means of the snap dome tripper, to move it past a given position, at which point the application layer goes "over center" to its second stable position. The result is thus a toggle-type-action and pressure applied to the application layer below a threshold sufficient to trigger the first change results in no change to the application layer's state.

In some of these embodiments, the transition from the second stable state to the first stable state is further configured to hinder any further transition from the first stable state to the second stable state. This means that the extraction device can only be used once and that when the application layer to which the needle carrier, and therefore the needles, are attached, returns to its first stable state, any further pressure applied on the snap dome tripper will not trigger another first change on the application layer. These embodiments are thus advantageously configured to minimize the risk of contaminating either the extracted fluid or another person.

For the uses of the extraction device to extract blood from a subject, it is beneficial to prevent that the subject's blood coagulates, i.e. turns from a liquid to a gel thus forming a clot that can block the channel of the needle. Therefore, in some embodiments the channel of the hollow needle is at least partially filled with an anticoagulant substance.

Puncturing the skin surface, especially if a plurality of hollow needles is used, can be hindered by the so called "bed-of-nails" effect, where the pressure is distributed between the needles such that the pressure exerted by each of them is not enough to puncture the skin surface. Therefore, in some embodiments of the present invention, the support structure comprises a guidance rail configured to exert a vibrating motion having a motion component in a direction substantially parallel to the surface skin, the vibrating motion configured to facilitate insertion of the needle into the skin. The vibrating motion, in the sense of this invention, refers to a vibrating movement in a direction substantially perpendicular to the movement of the needle towards and into the surface skin. In some embodiments, the guidance rail configured to guide the movement of the needle carrier in the direction substantially perpendicular to the skin surface comprises a straight first segment which lies substantially perpendicular to the needle carrier and a second segment having a zig-zag like shape. The second segment is closer to the skin surface than the straight first segment upon operation of the extraction device, and the second segment has a projected length amount on the direction of the straight first segment shorter than the length of the hollow needle. In this way the needles move in contact with the skin by moving in straight direction substantially perpendicular to the skin surface. After they have penetrated the skin, they keep moving in the same direction, but the guidance rails having a curved or zig-zag like segment, force the needle carrier to move also with an alternating lateral component substantially parallel to the skin surface, which favors the penetration of the needle down to a right depth for extracting the desired body fluid. In other embodiments the guidance rail and the needle carrier are made of different materials having different values of frictional resistance such as, but not limited to, rubber and metal. In other embodiments the materials of the guidance rail and the needle carrier have different surface structures that are advantageously configured to generate the vibrating motion upon operation.

Any of the embodiments of the body fluid extraction device of the second aspect of the invention can also be configured to provide also a testing function of a predetermined analyte or property of the body fluid.

These embodiments thus advantageously combine the decoupling of the application of a force to a body fluid extraction device from the actual piercing of the skin by the at least one needle of the body fluid extraction device of the second aspect with the improved transport and testing capability of the body fluid extraction device for extracting and testing a body fluid of the second aspect of the invention. To this end, embodiments of the body fluid extraction device of the second aspect that do not comprise a collection unit further include a collection chamber comprising a capillary wick configured to transport at least a fraction of the body fluid away from base end of the hollow needle. The embodiments that do comprise a collection unit further include a capillary wick arranged in the collection unit.

Furthermore, all of these embodiments further comprise a testing chamber comprising at least one testing unit that includes a respective reacting material configured to react in a predetermined manner to a predetermined analyte or property of the body fluid, a solution chamber, comprising a buffer solution and flow control means configured to control, in a first step, a first transfer of the buffer solution from the solution chamber to the collection unit, and in a second step a second transfer of the body fluid and the buffer solution from the collection unit to the testing chamber.

The additional features of the different embodiments of the body fluid extraction device of the first aspect may also be advantageously combined with the additional features of the different embodiments of the body fluid extraction device of the second aspect of the invention.

According to a third aspect of the present invention, a method for operating a body fluid extraction device for extracting body fluids through a skin surface is presented. The method comprises:
  placing the extraction device in contact with the skin surface, the extraction device having an outer side of a needle carrier facing the skin surface
  exerting a predetermined activation force on a snap dome tripper, the activation force corresponding at least to the force required to push the hollow needle into the skin surface
  inducing a snap movement of the needle carrier relative to the support structure;
  collecting the extracted body fluid in a collection unit; and
  detaching the extraction device from the skin surface once a sufficient amount of body fluid has been extracted.

The method of the third aspect of the present invention shares the advantages of the body fluid extraction device of the second aspect of the present invention and any of its embodiments. In particular, the method enables the use of a body fluid extraction device where the insertion of the needle does not solely depend on the pressure applied by the user.

In the following, additional embodiments of the method of the third aspect will be described.

In one embodiment, the method of the third aspect further comprises detaching a sealing layer connected to the needle carrier holder prior to placing the extraction device in contact with the skin surface.

In another embodiment, the method further comprises conditioning the skin by rubbing an antiseptic material located on the sealing layer on the skin surface prior to placing the extraction device in contact with the skin surface It shall be understood that the body fluid extraction devices of claims 1, and 10 and the method for operating a body fluid extraction device of claim 24 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

BRIEF DESCRIPTION OF THE DRAWINGS

FIG. 7 shows a schematic diagram of a cross section of another embodiment of a body fluid extraction device.

FIG. 9 shows a flow diagram of an embodiment of a method for operating a body fluid extraction device.

DETAILED DESCRIPTION OF THE EMBODIMENTS

Figure 1:
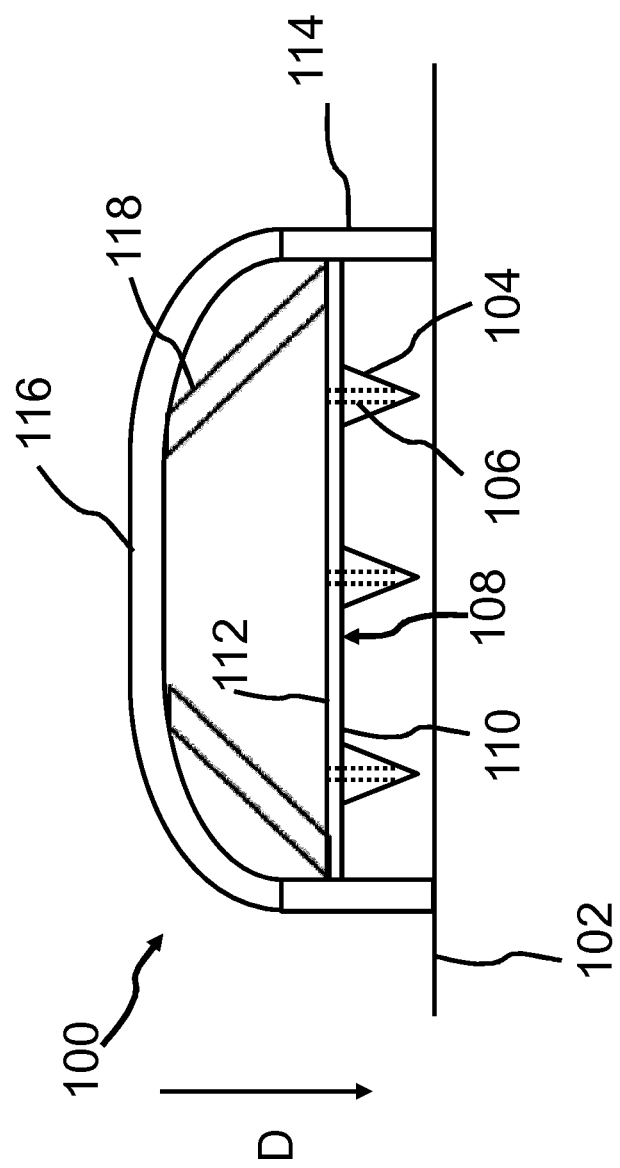
FIG. 1 shows a schematic diagram of a cross section of an embodiment of a body fluid extraction device.

FIG. 1 shows a diagram of a cross section of an exemplary embodiment of a body fluid extraction device 100 for extracting body fluids through a skin surface 102. FIG. 1 depicts the situation before an extraction of body fluids has taken place. The extraction device 100 comprises hollow needles 104 having a base end and a tip and a channel 106 linking the base end and the tip in fluid communication. The hollow needles 104 are attached or integrated to a needle carrier 108 which has an outer side 110 configured to face the skin surface upon operation of the extraction device, and an inner side 112 opposite to the outer side 110. Furthermore, the needle tip extends out of the outer side of the needle carrier. The extraction device also comprises a support structure 114 connected to the needle carrier 108 and configured to allow a relative movement of the needle carrier relative to the support structure in a direction D substantially perpendicular to the skin surface 102. Further, the extraction device comprises a snap dome tripper 116, which is connected to the support structure by connection structures 118, and which is arranged and configured to induce a snap movement of the needle carrier relative to the support structure.

Figure 2:
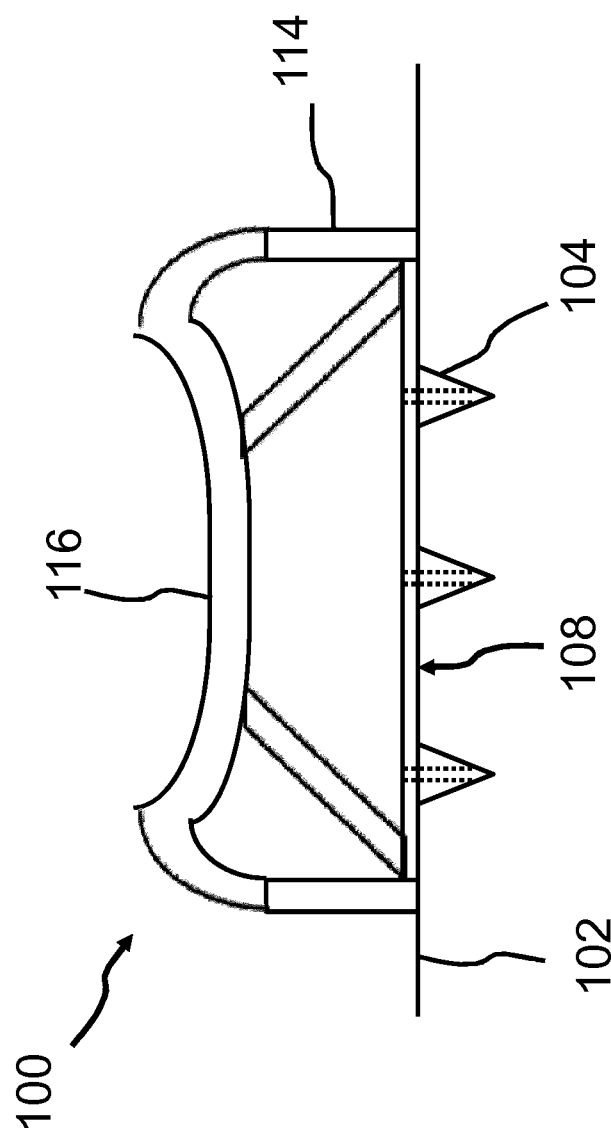
FIG. 2 shows a schematic diagram of a cross section of an embodiment of a body fluid extraction device upon operation.

FIG. 2 shows the body fluid extraction device 100 upon operation. A user has applied amount of force on the snap dome tripper 116 (e.g. by placing his finger on the snap dome tripper and pushing it downwards in the direction D, i.e. towards the skin surface 102), thereby inducing a snap movement that has facilitated the insertion of the needles 104 into the subject's skin. The needle carrier 108, which is connected with the snap dome tripper 116 by means of connection structures 118, is allowed to move relative to the support structure 114. The snap dome tripper comprises, in this exemplary embodiment, a dome-shaped applicator such as a monostable clicker which, after applying a predetermined amount of force, snaps to a state in which it remains for a predetermined amount of time span. Both the predetermined amount of force and the predetermined amount of time span are parameters that can be configured or set during the fabrication process of the extraction device, since they mainly depend of the choice of materials and dimensions of the snap dome tripper. After the predetermined time span has lapsed, the snap dome tripper returns to its stable state (as depicted in FIG. 1), thus facilitating the removal of the needles from the skin surface.

The skin of an adult has an average thickness of about 2 millimeters. The outermost layer of the skin is the stratum corneum, mostly consisting of dead cells. Its thickness varies from roughly 10 micrometers to over 150 micrometers depending on the body part. Situated below the stratum corneum is the epidermis, with a thickness ranging approximately from 30 to 130 micrometers. The dermis, which holds abundant blood vessels and a few nerve endings lies below the epidermis and has a thickness of approximately 800 micrometers to 1.5 millimeters.

The needles are, in some embodiments, microneedles with lengths sufficient to penetrate the stratum corneum and pass into the epidermis, but not penetrate through the epidermis and into the dermis in applications where it is desirable to minimize pain to the subject. The length of the microneedles is typically below 1 mm. In some embodiments the length is below 500 micrometers. The outer diameter of the needles is in some embodiments smaller than 300 micrometers. In other embodiments, the microneedles are configured as an array of needles. Such an array includes, in different embodiments, microneedles having different lengths, cross sectional shapes, orientations, inner diameters, outer diameters and spacing between the different needles. In some embodiments the microneedle array has an area below 4 $cm^2$, in other embodiments the area of the microneedle array is below 2 $cm^2$. The size and shape of the array depend on the choice of the probing place of the skin surface. The probing place may be, but is not limited to, forearm, wrist, leg, earlobe, the inner part of the nose, etc.

Figure 3:
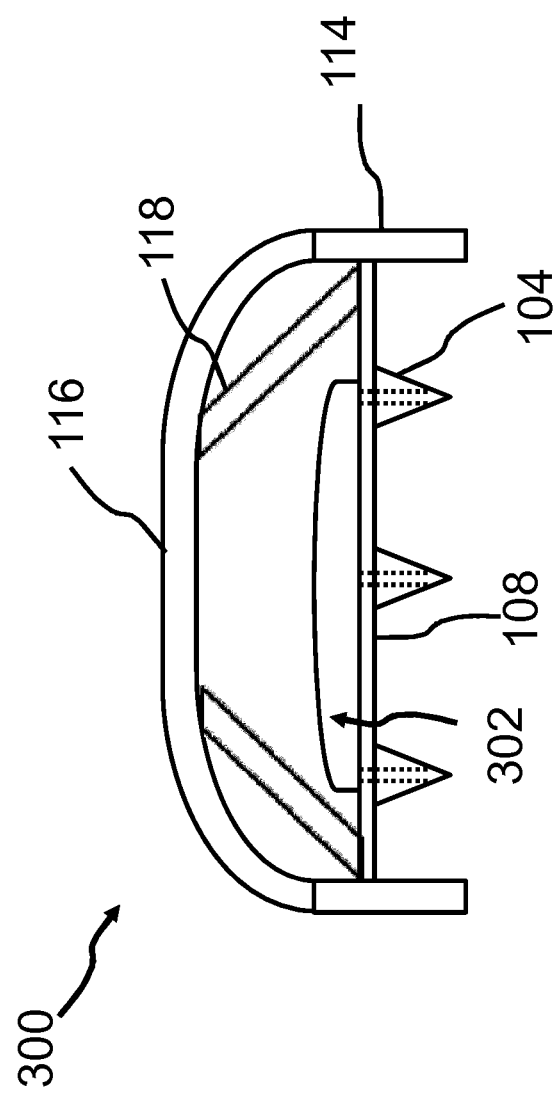
FIG. 3 shows a schematic diagram of a cross section of another embodiment of a body fluid extraction device.

FIG. 3 shows another exemplary embodiment of a cross section of a body fluid extraction device 300, with reference also to FIG. 1. The extraction device 300 further comprises a collection unit 302 configured to collect the body fluid, the collection unit being in fluid communication with the base end of the hollow needle 104 at the inner side of the needle carrier 108. The body fluid is extracted by capillary action. In some embodiments the extraction is enhanced by the presence of an absorbing material located within the collection unit and being in fluid communication with the base end of the needle 104. In other embodiments, the extraction is also enhanced by the presence of a pressure gradient. The collection chamber is in these cases configured to have a lower pressure than the atmospheric pressure and acts as a pump for the body fluids, which get sucked into the collection unit aided by the pressure gradient. In other embodiments, the extraction device comprises several independent collection units. The fluids collected in each one of them can be therefore used for different purposes. In some embodiments the extraction devices are configured to extract a volume of body fluids of at least 10 microliters. In some embodiments, the one or more collection units 302, or a subset of the collection units, in case a plurality of them pare present, comprise an absorbing material in fluid communication with the base end of the needle. In some of these embodiments, cellulosic or fiber based materials are used. In other embodiments superabsorbing polymers or hydrogels are used. In some embodiments, the collection unit comprises a material that reacts in predetermined form with a given constituent or characteristic of the body fluid. These embodiments are therefore advantageously configured to test the presence or the amount of that given constituent or the characteristic of the body fluid. The constituent of the body fluid may be, but is not limited to, a given chemical element, ion or molecule. A non-limiting example of a characteristic of the body fluid that is analyzed in some embodiments is the pH-value of the extracted body fluid.

Figure 4:
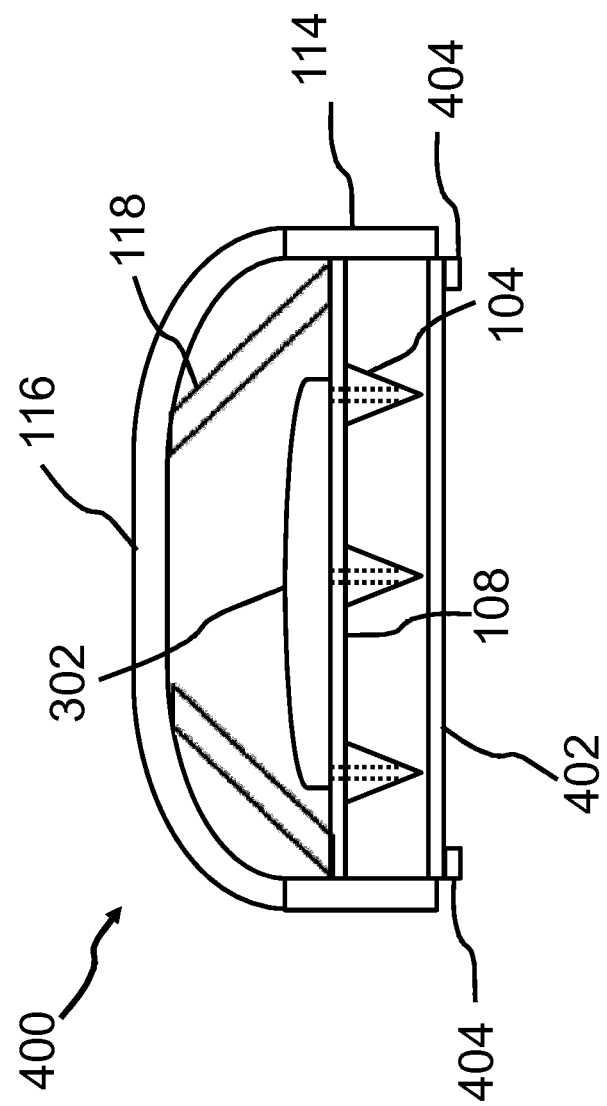
FIG. 4 shows a schematic diagram of a cross section of another embodiment of a body fluid extraction device.

FIG. 4 shows a diagram of a cross section of a body fluid extraction device 400, also with reference to the previous figures. This extraction device comprises a protective membrane 402 that is connected to the support structure 114 and which is configured to cover the outer side of the needle carrier, and wherein a portion of the protective membrane 402 comprises and adhesive layer 404 configured to attach the extraction device to the skin surface. The protective membrane is in some embodiments configured to keep the needles sterile. The protective membrane is in some embodiments made of polypropylene. In other embodiments the protective membrane is made of polyamide. Other embodiments have protective membranes made of other materials such as, but not limited to, polyethylene. In some embodiments the outer side of the protective membrane is impregnated with a material configured to reduce the elasticity of the skin and thus to facilitate the insertion of the needles. In some embodiments where the extraction of the body fluid is further facilitated by the presence of a pressure gradient, the protective membrane is also configured to maintain the low pressure conditions inside the hollow needles and the collection unit.

In some advantageous embodiments, the adhesive layer is not located at the places where the needles 104 pierce the protective layer 402. This avoids that part of the adhesive material is introduced together with the needles into the skin. In some particularly advantageous embodiments, the adhesive layer is located at a perimeter of a most outer section of the protective membrane. In other embodiments, the adhesive layer is further configured to stretch the skin upon operation of the extraction device and thus to facilitate the insertion of the needles 104.

Figure 5:
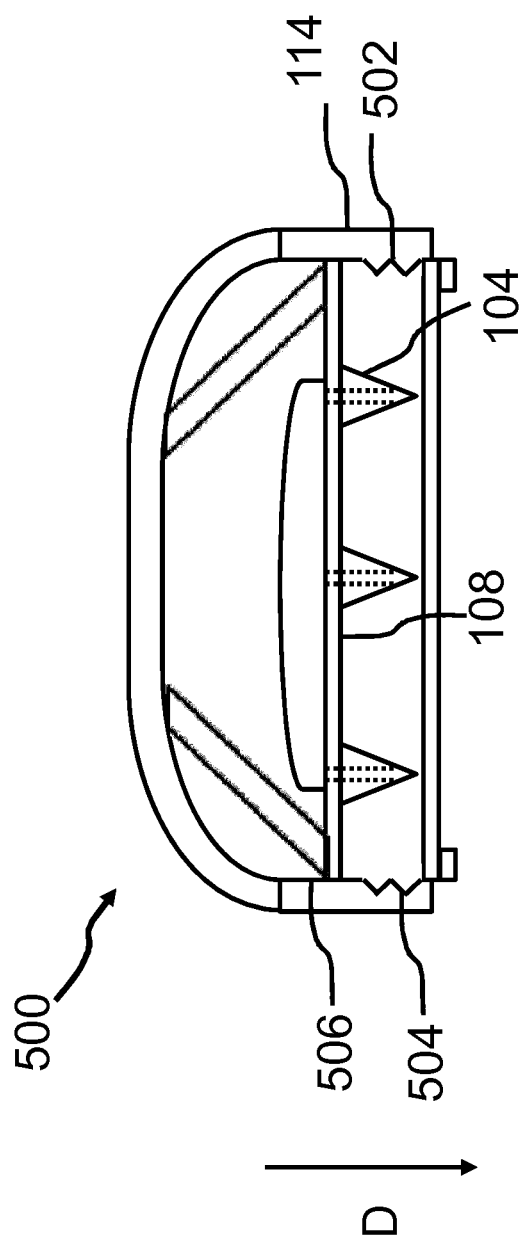
FIG. 5 shows a schematic diagram of a cross section of another embodiment of a body fluid extraction device.

Researchers have carefully observed the skin penetration process of mosquitoes. The oscillation of two needle-like maxillae can facilitate the penetration of the labrum. FIG. 5 shows a diagram of a cross section of a body fluid extraction device 500 which is configured to mimic the vibration performed by the mosquitoes upon extracting blood and to further avoid the bed-of-nails effect. This effect happens when the weight or pressure applied is evenly distributed between the needles in the microneedle array, and the pressure exerted by each nail is not enough to puncture the subject's skin. The support structure 114 of the extraction device 500 comprises a guidance rail configured 502 to guide the needle carrier 108 in the movement of the needle carrier in the direction D substantially perpendicular to the skin surface. The guidance rail comprises a straight first segment 506 which lies substantially perpendicular to the needle carrier 108 and a second segment 504 having a zig-zag like shape. The second segment is therefore closer to the skin surface that the straight first segment upon operation of the extraction device. The second segment has a projected length amount on the direction of the straight first segment shorter than the length of the hollow needle. Thus, upon operation, the needles move in a straight movement towards the skin of the subject and slightly press its surface. Piercing and entering the skin is then facilitated by the zig-zag movement induced by the presence of the second segment of the guidance rail, which has a zig-zag like shape. Zigzag like shape and movement should be understood in the frame of this invention as a wavy-like shape or movement between two imaginary substantially parallel lines.

Figure 6:
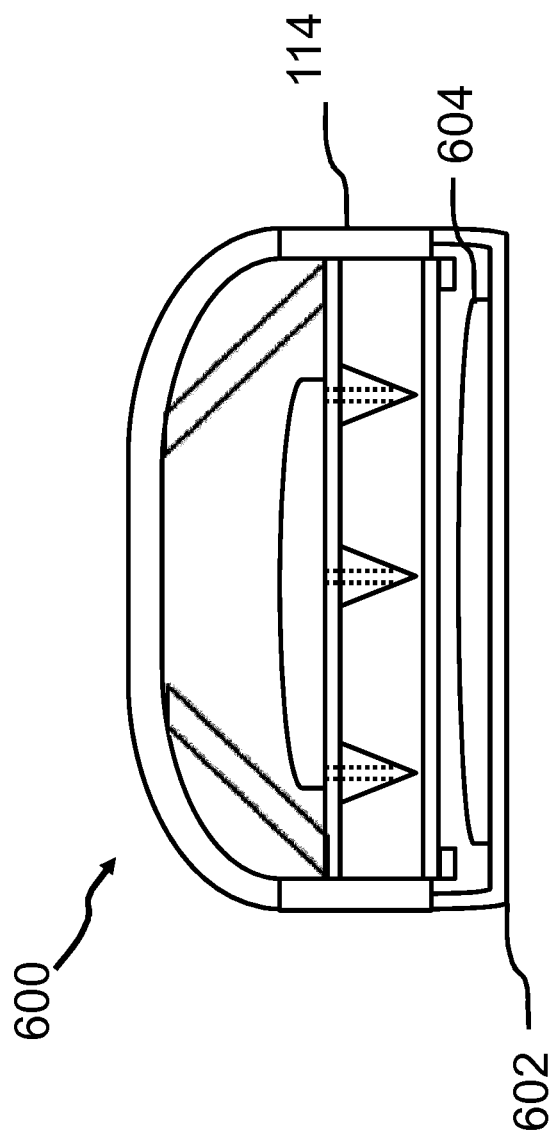
FIG. 6 shows a schematic diagram of a cross section of another embodiment of a body fluid extraction device.

FIG. 6 represents an exemplary cross section of another embodiment of an extraction device 600. The extraction device 600 further comprises a detachable sealing layer 602 connected to the support structure 114. The sealing layer has an internal side facing the outer side of the needle carrier and an external side opposite to the internal side. The sealing layer is configured to cover hermetically the protective membrane. Furthermore, the extraction device 600 comprises a skin conditioning layer 604 comprising an antiseptic material, the skin conditioning layer being attached to the internal side of the sealing layer 602. The detachable layer is configured to avoid external contamination of the needles and the collection unit. The sterile extraction device is thus advantageously kept sterile at least until the sealing layer is removed. Furthermore, in some embodiments, hermetically sealing the extraction device helps to maintain the low pressure conditions inside the extraction device, in embodiments where the protective membrane is not capable to maintain those conditions until the extraction device is used.

Before the extraction device is used, the user detaches the detachable sealing layer 602 which keeps the extraction device sterile and then conditions his or her skin using the antiseptic material comprised in the skin conditioning layer 604. In some embodiments the antiseptic material comprises alcohols, such as, but not limited to ethanol, 1-propanol, isopropanol or mixtures thereof. In other embodiments, quaternary ammonium compounds are used. In other embodiments iodine-based antiseptic materials are used. Other embodiments comprise other skin-compatible antiseptic materials. The skin conditioning layer can be also used after extracting the body fluids to rinse the skin surface where the extraction device has been applied.

FIG. 7 shows a cross section of another embodiment of an extraction device 700. The extraction device comprises an expandable material 702 located between the outer side of the needle carrier and the protective membrane. This expandable material is configured to expand, within a predetermined expansion time span from an initial volume amount to a final volume amount. The final volume amount is configured to cover the tip of the hollow needles, thus rendering them useless and increasing the safety of the extraction device after use. In some embodiments the expandable material is a material that reacts to a pressure stimulus, expands to a final volume and hardens. The pressure stimulus is in some embodiments provided by the user applying and pressing the extraction device onto the skin surface. In other embodiments the expandable material results from mixing to materials that are on their own not expandable. Pressing the extraction device 700 against the skin brings them into contact and triggers the expansion. Other embodiments comprise expandable materials that react with a reacting agent (such as, but not limited to, air) that triggers the expansion and subsequent hardening of the expandable material. The predetermined expansion time span is sufficiently long to allow for a complete extraction of the required amount of body fluids. In some embodiments the expansion time span is also sufficiently short to avoid having to manipulate the extraction device after its use with the needles being accessible, i.e. needles tips not covered by the expandable material. In other embodiments, the expandable material, upon expanding from its initial to its final volume, helps to extract the needle from the skin.

Figure 8A:
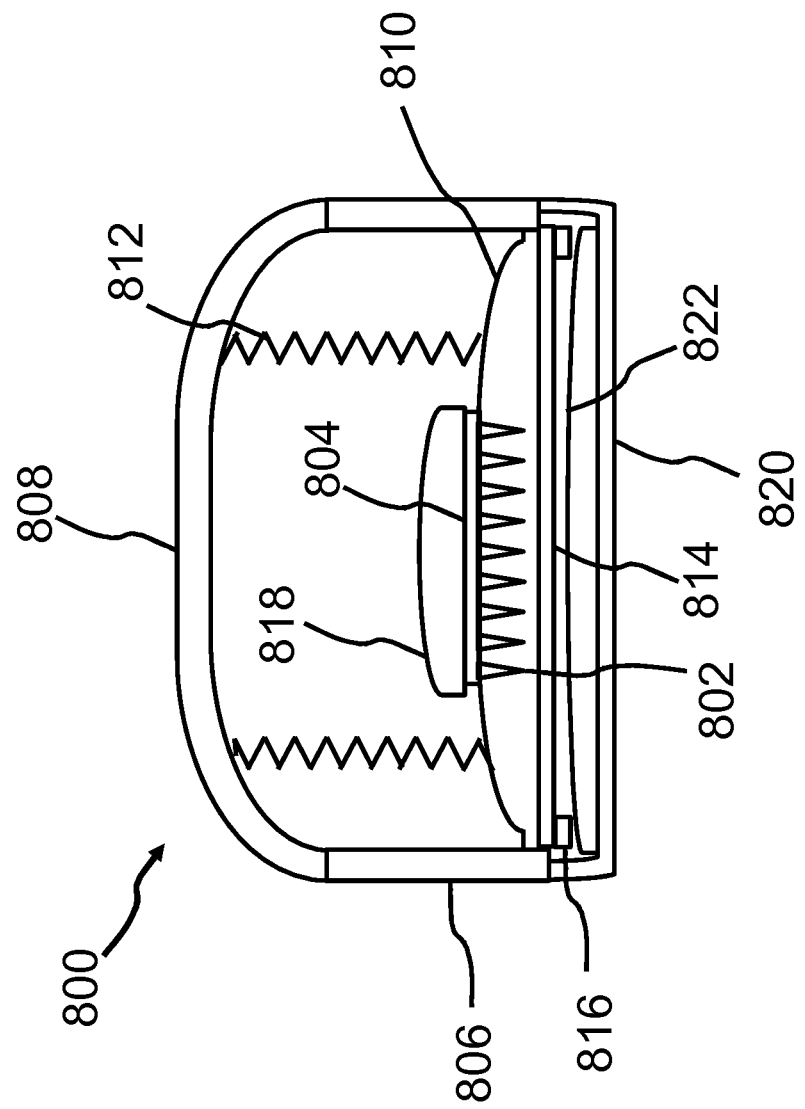
FIG. 8a shows a schematic diagram of a cross section of another embodiment of a body fluid extraction device.
Figure 8B:
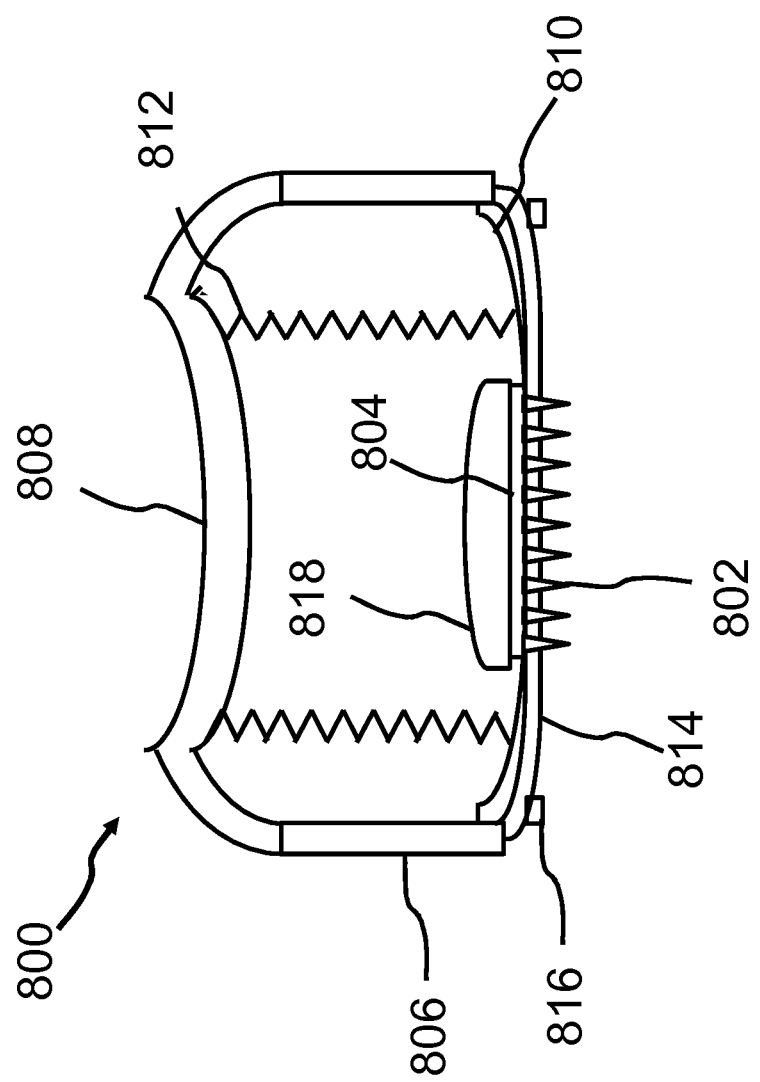
FIG. 8b shows a schematic diagram of a cross section of another embodiment of a body fluid extraction device upon operation.

FIG. 8a shows a cross section of another exemplary embodiment of a body fluid extraction device 800, whereas FIG. 8b shows the same extraction device 800 upon operation. The extraction device 800 comprises a plurality of hollow needles 802 integrated to a needle carrier 804, which is connected to a support structure 806. A snap dome tripper 808, also connected to the support structure 806, is configured to induce a snap movement of the needle carrier relative to the support structure. In order to do that, the snap dome tripper 808 is connected to an application layer 810 by a connection structure 812, which, in some embodiments is a spring like structure. The application layer has a first stable state and a second stable state, i.e., the application layer is a bistable material and the system is said to be "over center". Pressure is applied on the application layer 810, by means of the snap dome tripper 808, to move it past a given position, at which point the application layer goes "over center" to its second stable position. The result is thus a toggle-type-action and pressure applied to the application layer below a threshold sufficient to trigger the first change results in no change to the application layer's state.

FIG. 8*a* represents the application layer 810 in its first stable state. By applying a sufficient amount of external pressure on the snap dome tripper 808, the application layer snaps from the first stable state to the second stable state. At this point the user stops to apply pressure on the extraction device and the snap dome tripper 808 starts to return to its original state, i.e. the first stable state. FIG. 8*b* represents the extraction device during operation, with the application layer in its second stable state, and while the snap dome tripper 808 is returning to its original state. In a transition of the application layer from its first to its second stable state, the predetermined activation force corresponding to the force required to push the hollow needles 802 into the skin surface is exerted. i.e., the needle carrier has moved in a direction D towards the skin surface has pierced the protective layer 814 and has entered the skin surface to which the extraction device is attached to with help of the adhesive layer 816. The extracted body fluid is collected in a collection unit 818. Meanwhile, the connection structure 812 is returning to its original state thereby exerting a force on the activation layer in a direction away from the subject's skin. After an extraction time span has lapsed, the connection structure triggers a transition from the second stable state to the first stable state. This transition is configured to facilitate an extraction of the hollow needles 802 from the skin surface. The extraction time span thus depends on the material and shape of the connection structure 812 and the activation layer, and it is advantageously configured to allow the extraction of a sufficient amount of body fluid before the transition from the second stable state to the first stable state takes place. Before using the extraction device, the user has conveniently removed the sealing layer 820 and conditioned the subject's skin using the antiseptic material comprised in the ski conditioning layer 822. In some embodiments, the sealing layer can be put back in its original place to ensure that an accidental access to the needles is further hindered. Other embodiments also include the expandable material which, after operation, is configured to cover the tips of the needles so as to minimize the risks of contamination or infection. In other embodiments, the transition from the second stable state to the first stable state is further configured to hinder any further transition from the first state to the second state. This means that in these embodiments, the device can only be operated once, thus limiting the risks of contaminating the extracted body fluid and/or another user or subject. In some embodiments this effect is achieved by decoupling the connection structure 812 from either the snap dome tripper 808 or the application layer 810.

FIG. 9 shows a flow diagram of an embodiment of a method 900 for operating a body fluid extraction device. In a first step 902, the user removes a detachable sealing layer, and then, in a step 904 conditions a region of the skin using an antiseptic material. Later, in a step 906, the user places the extraction device in contact with the skin surface with the outer side of a needle carrier facing the skin surface. The extraction device attaches to the skin surface with help of an adhesive layer. Once adhered, a predetermined activation force on an arched or dome-shaped applicator is exerted in a step 908. This activation force corresponds to the force required to push the hollow needle into the skin surface and it induces a snap movement of a needle carrier relative to a support structure is induced. At least one needle enters the skin in a step 910, following the inducement of the snap movement. The extracted body fluid is then collected in a collection unit under step 912. Once a sufficient amount of fluid is collected, the extraction device is detached from the skin in a step 914.

Figure 10:
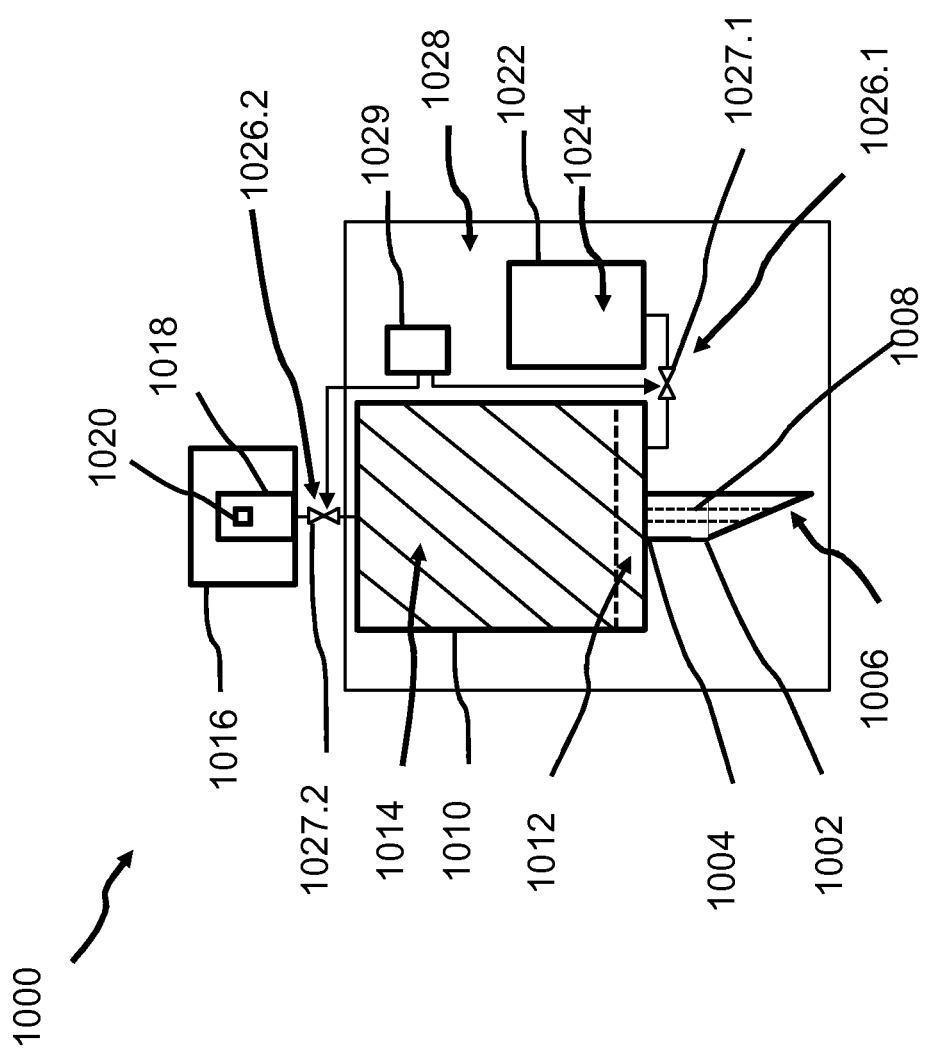
FIG. 10 shows a schematic diagram of an embodiment of a body fluid extraction device for extracting and testing a body fluid

FIG. 10 shows a schematic representation of an exemplary embodiment of a body fluid extraction device (1000) for extracting a body fluid and for testing at least one predetermined analyte or property of the body fluid. The body fluid extraction device 1000 comprises one hollow needle 1002 that has a base end 1004 and a tip 1006 and a channel 1008, represented by a dashed line, linking the base end 1004 and the tip 1006 in fluid communication. The body fluid extraction device further comprises a collection chamber 1010 that has an input end 1012 in fluid communication with the channel 1008 of the hollow needle 1002. The collection chamber contains a capillary wick 1014 that is configured to transport at least a fraction of the body fluid away from the input end 1012. Furthermore, the body fluid extraction device 1000 comprises a testing chamber 1016 that has one testing unit 1018 that includes a reacting material 1020 configured to react in a predetermined manner to a predetermined analyte or property of the body fluid. The body fluid extraction device also comprises a solution chamber 1022 that includes a buffer solution 1024. Finally, flow control means 1026.1 and 1026.2 control, in a first step, a first transfer of the buffer solution from the solution chamber to the collection chamber, and, in a second step, a second transfer of the body fluid and the buffer solution from the collection chamber to the testing chamber respectively. In this exemplary body fluid extraction device, the flow control means is a first valve 1027.1 and a second valve 1027.2. Both valves are externally controllable by a respective first and second control signal (represented by an arrow). The control signal is in some embodiments generated by an embedded processing unit 1029. In other embodiments the first and second control signals are provided by an external processing unit (not shown). Other possible flow control means will be described with respect to FIGS. 11 and 12 but can also be used in replacement of the flow control means 1026.1 and 1026.2.

Therefore, upon operation, the hollow needle 1002 of the body fluid extraction device 1000 is inserted into a body and enters in contact with a body fluid, such as for example, blood circulation inside a blood vessel. Through capillarity, the body fluid travels inside the channel 1008 from the tip 1006 to the base end 1004 of the hollow needle 1002. The channel 1008 is in fluid communication with the input end 1012 of the collection chamber, so the body fluid enters the collection chamber 1010 through the input end 1012. The capillary wick 1014 that is inside the collection chamber 1010 aids in transporting at least part of the body fluid away from the input end, and towards the testing chamber 1016. The transport of the body fluid is further enhanced by the buffer solution 1024 included in the solution chamber 1022. The flow control means 1026.1 controls, in a first step, the transfer of the buffer solution 1024 from the solution chamber 1022 to the collection chamber 1010. In this particular body fluid extraction device 1000, the buffer solution 1024 is transferred to the collection chamber 1010 via the input end 1012. The presence of the buffer solution 1024 in the collection chamber 1010 enhances the transport of the bodily fluid, now mixed with the buffer solution away from the input end 1012 and towards the testing chamber 1016. The flow control means 1026.2 controls, in a second step, the second transfer. The second transfer refers to a transfer of the bodily fluid and the buffer solution from the collection chamber 1010 to the testing chamber 1016, where the predetermined analyte or property of the body fluid is tested by the reacting material 1020 comprised by the testing unit 1018.

In this particular body fluid extraction device 1000, the hollow needle 1002, the collection chamber 1010 and the solution chamber 1022 are arranged inside a sealed chamber, wherein the testing chamber is arranged outside the sealed chamber 1028. The sealed chamber 1028 and the testing chamber 1016 are configured to be brought into fluid communication upon transferring the body fluid and the buffer solution from the collection 1010 chamber to the testing chamber 1016. The presence of the sealed chamber 1028 is advantageous in cases where it is necessary to preserve a sterile condition of the hollow needle, the collection chamber and the solution chamber. The testing chamber 1016 may therefore be in a non-sterile condition since it is separated from the sealed chamber 1028 at least prior to the use of the body fluid extraction device.

Figure 11:
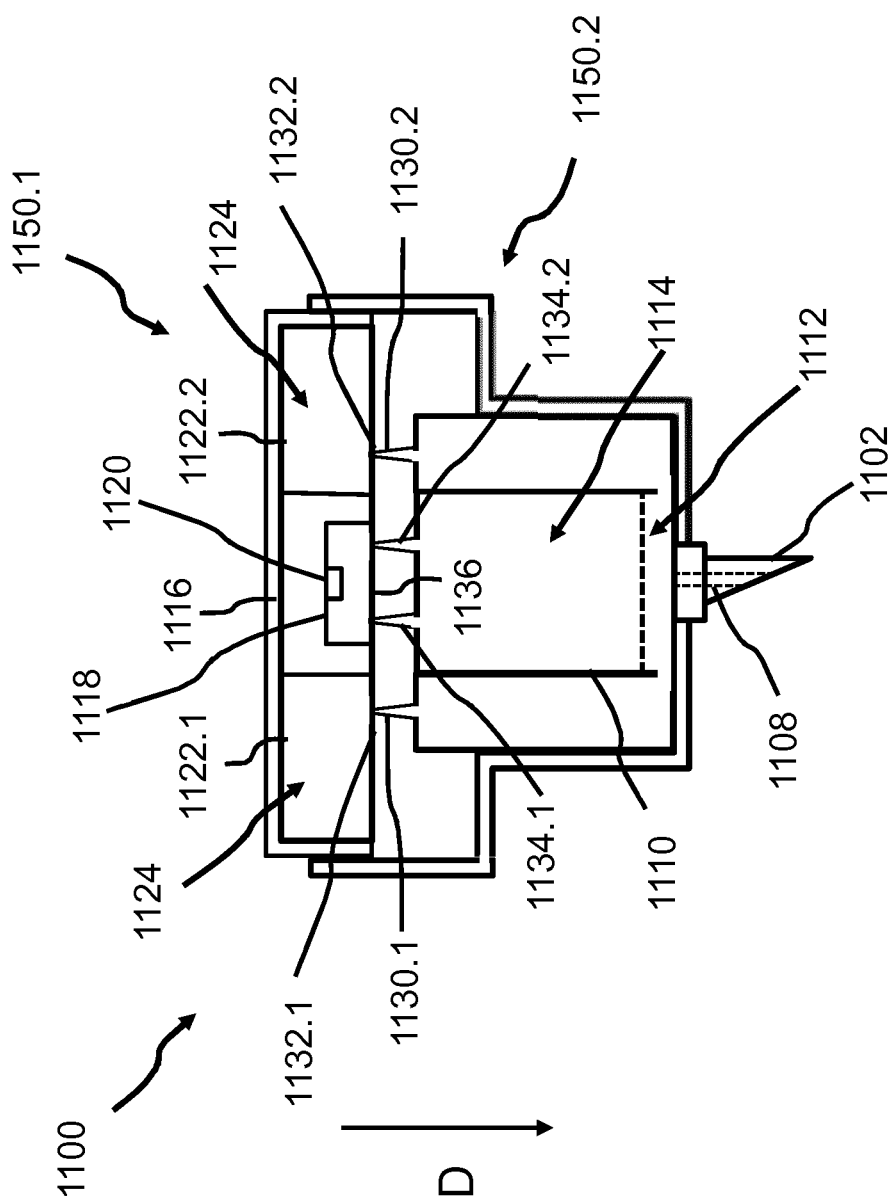
FIG. 11 shows a schematic diagram of another embodiment of a body fluid extraction device for extracting and testing a body fluid

FIG. 11 shows a schematic representation of another embodiment of a body fluid extraction device 1100 for extracting and testing a body fluid. Reference numerals of structural elements of the body fluid extraction device 1100 that correspond to structural elements of the body fluid extraction device 1000 of FIG. 10 differ only in their first two digits, which are "11" instead of "10". Therefore, for brevity of the present description, reference is also made to the description of FIG. 10 for details of these structural elements. The following description mainly concentrates on features distinguishing the two embodiments from each other. The device 1100 comprises a hollow needle 1102 with a channel 1108 that is in fluid communication with an input end 1112 of a collection chamber 1110. A testing chamber 1116 includes a testing unit 1118 that comprises a reacting material 1120. A solution chamber comprises two sub-chambers 1122.1 and 1122.2 both of which are filled with a buffer solution 1124. The flow control means comprise in this exemplary body fluid extraction device, two first cannulas 1130.1 and 1130.2. Other body fluid extraction devices that are not shown comprise one or more than two first cannulas. The two first cannulas 1130.1 and 1130.2 are configured to pierce a respective first pierceable wall section 1132.1 and 1132.2 of the solution chamber. When the first pierceable wall sections 1132.1 and 1132.2 are pierced by the respective first cannulas 1130.1 and 1130.2, the solution chamber (i.e. the two sub-chambers 1122.1 and 1122.2 in this particular embodiment) is brought into fluid communication with the input end 1112 of collection chamber 1110.

Furthermore, the body fluid extraction device 1100 comprises two second cannulas 1134.1 and 1134.2 that are configured to pierce a second pierceable wall section 1136 of the testing chamber 1116. When the second pierceable wall sections 1136 is pierced by the second cannulas 1134.1 and 1134.2, the collection chamber is brought into fluid communication with the testing chamber 1116, enabling a transfer of the body fluid and the buffer solution to the testing unit so that the reacting material 1120 can get in contact with the body fluid and the buffer solution.

In an exemplary operation for extracting and testing a body fluid such as blood from a capillary, the needle 1102 is put in contact with the skin of a subject. Pressure is applied so as to insert the needle through the skin. Blood starts to flow through the channel 1108 towards the collection chamber 1110, aided by capillarity effects. At the same time, the pressure applied causes the first cannulas 1130.1 and 1130.2 to pierce the first pierceable wall sections 1132.1 and 1132.2 so that the collection chamber (in this case the two sub-chambers 1122.1 and 1122.2 that form the collection chamber) are brought in fluid communication with the collection chamber 1110 via the input end 1112. A mixture of the body fluid and the buffer solution 1124 is transported by the capillary wick (not shown) comprised inside the collection chamber 1110 away from the input end towards the testing chamber 1116. The same pressure applied causes the second cannulas 1134.1 and 1134.2 to pierce the second pierceable wall section 1136 of the testing chamber 1116 thus bringing the collection chamber 1110 and the testing chamber 1116 in fluid communication.

In order to achieve this effect, some embodiments comprise two parts that are configured to allow a movement of one of the two parts relative to the other part. For example in the body fluid extraction device 1100 a first part 1150.1 of the two parts comprises the solution chamber (1122.1 and 1122.2) and the testing chamber, whereas a second part 1150.2 of the two parts comprise the needle 1102, the collection chamber 1110 and the flow control means 1130.1, 1130.2, 1134.1 and 1134.2. Applying a pressure on the first part 1150 in the direction D indicated in FIG. 11 triggers a piercing of the first and second pierceable wall sections (1132.1 and 1132.2, and 1136 respectively) and, if the device is properly positioned for operation, an insertion of the needle 1102 into a subject (not shown).

Figure 12:
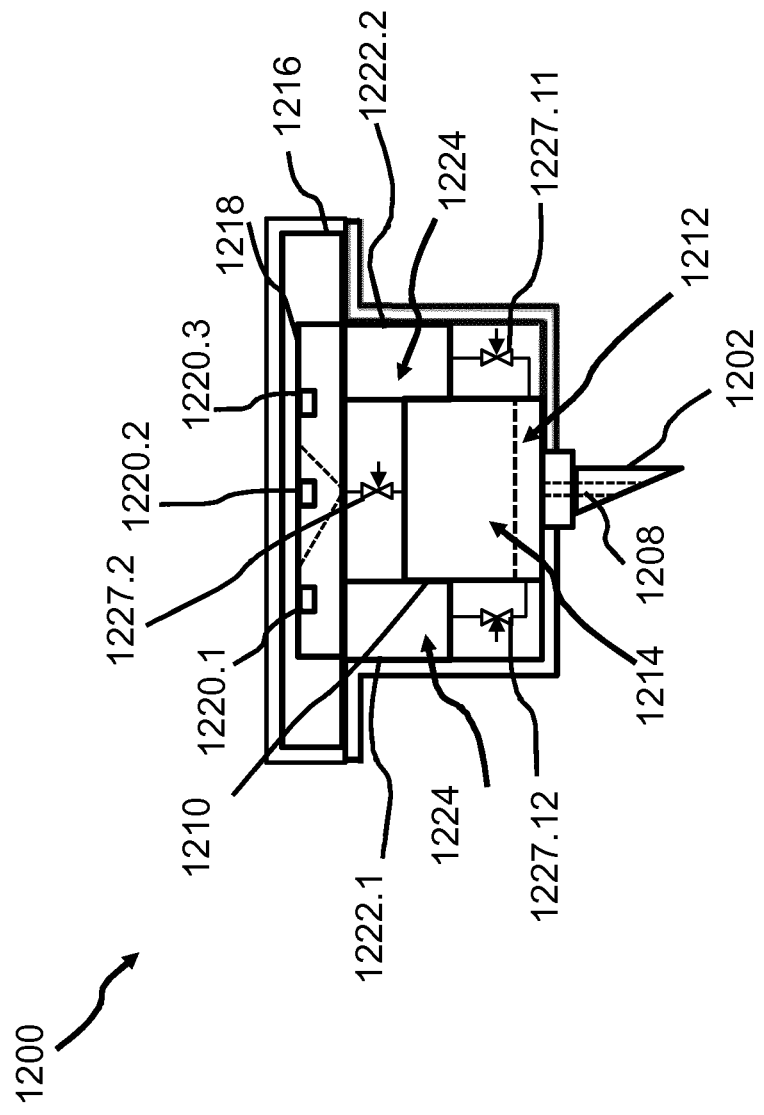
FIG. 12 shows a schematic diagram of another embodiment of a body fluid extraction device for extracting and testing a body fluid

FIG. 12 shows another alternative embodiment of a body fluid extraction device 1200 for extracting and testing a body fluid. Reference numerals of structural elements of the body fluid extraction device 1200 that correspond to structural elements of the body fluid extraction device 1000 of FIG. 10 and 1100 of FIG. 11 differ only in their first two digits, which are "12" instead of "10", and "11" respectively. Therefore, for brevity of the present description, reference is also made to the description of FIGS. 10 and 11 for details of these structural elements. The following description mainly concentrates on features distinguishing the two embodiments from each other.

In this particular body fluid extraction device 1200, the flow control means comprise two first valves 1227.11 and 1227.12 that control, in dependence on a predetermined first control signal, a first fluid connection between the respective sub-chamber 1222.1 and 1222.2 of the solution chamber and the input end 1212 of the collection chamber 1210. The flow control means also comprise a second valve 1227.2 that controls, in dependence on a predetermined second control signal, a second fluid connection between the collection chamber 1210 and the testing chamber 1216. The first and the second control signals are in some embodiments provided by an embedded processing unit (not shown). In other embodiments, the first and second control signals are provided by an external processing unit (not shown).

Additionally, the testing chamber comprises three testing units (indicated by the dashed lines) that include a respective reacting material 1220.1, 1220.2 and 1220.3. Each of the reacting materials is configured to react in a predetermined manner to a respective predetermined analyte or property of the body fluid.

Any of the body fluid extraction devices 1000, 1100 and 1200 described with reference to FIGS. 10-12 may further include a hollow needle having an inner wall of the channel the is at least partially covered by a covering layer comprising a hydrophilic material. These devices are advantageously configured to extract more fluid per unit time, than those that do not include a covering layer comprising a hydrophilic material.

Figure 13:
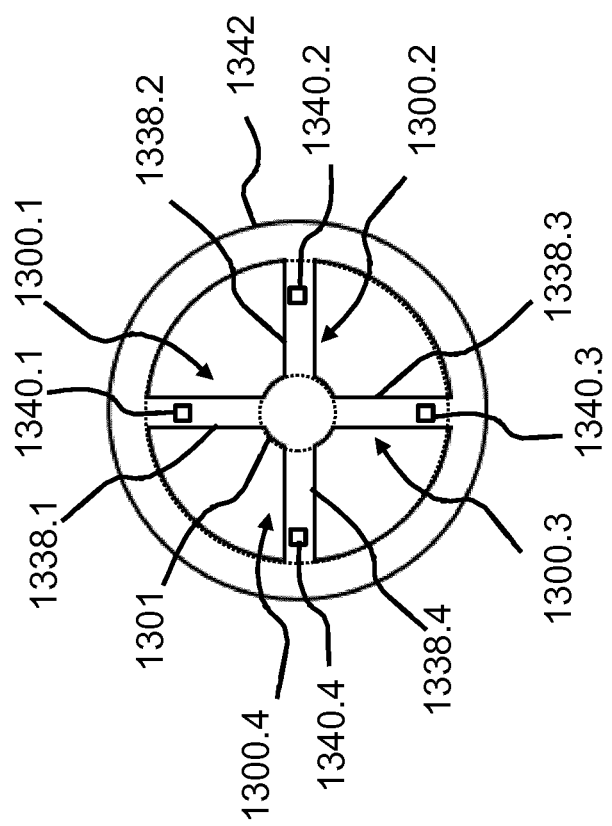
FIG. 13 shows a schematic diagram of a plurality of testing units sharing a common sample pad.

In the body fluid extraction devices 1000, 1100 and 1200 described with reference to FIGS. 10-12, the testing chamber can comprise more than one testing unit. This is shown in FIG. 13, where four testing units 1300.1, 1300.2, 1300.3 and 1300.4 are presented. The four testing units, that form four distinct lateral flow assay units, share a common sample pad 1301 that is configured to adsorb the bodily fluid and the buffer solution after the second transfer (i.e. the common sample pad is arranges to receive the bodily fluid and the buffer solution from the collection chamber after the second step). From a common centre formed by the common sample pad 1301, four testing capillary wicks 1338.1, 1338.2, 1338.3 and 1338.4 extend radially. A respective reacting material 1340.1, 1340.2, 1340.3 and 1340.4 are arranged on each testing capillary wick.

Figure 14:
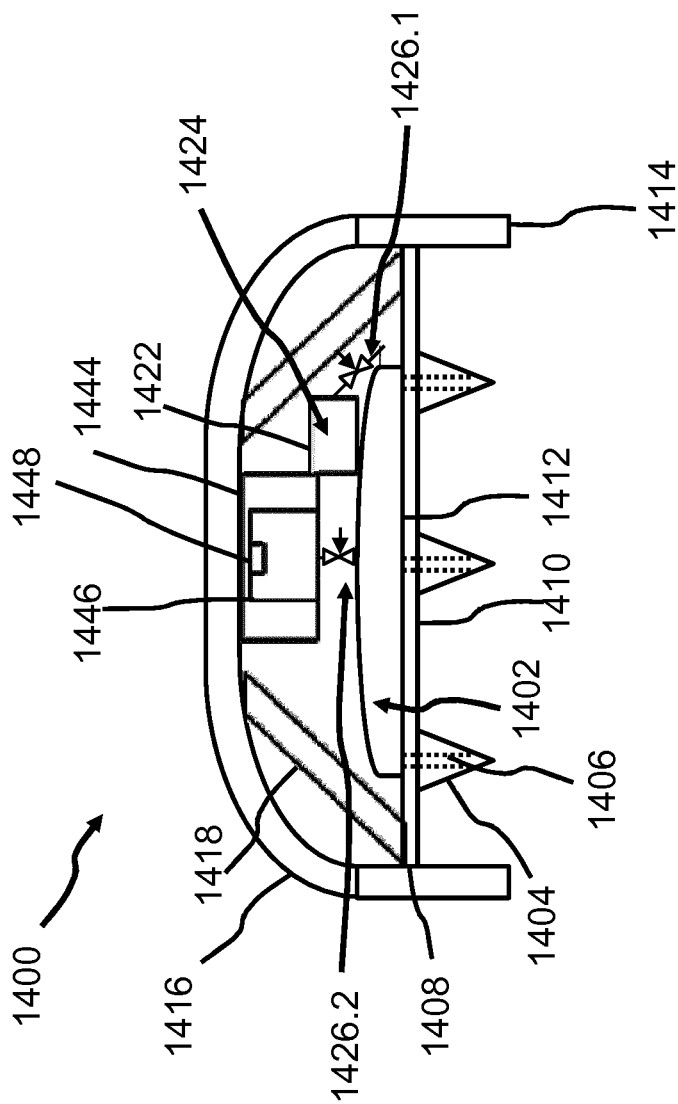
FIG. 14 shows a schematic diagram of another embodiment of a body fluid extraction device for extracting and testing a body fluid that includes a snap dome tripper.

Upon operation, and after the second transfer has taken place in the second step controlled by the flow control means, the body fluid and the buffer solution flow from the common sample 1301 pad along the testing capillary wicks 1338.1-4 passing though the respective reacting material 1340.1-4 based on the capillary force of the testing capillary wicks. Additionally, in some embodiments, and in order to maintain this flow movement, an absorbent pad 1342 is attached at the end of the testing capillary wicks. The role of the absorbent pad 1342 is to wick the excess body fluid and buffer solution and prevent backflow of the body fluid and buffer solution. In this particular example, the absorbent pad has a circular form, but other designs are possible. Also the number of testing units that can be included is variable and limited by geometrical and fabrication aspects. FIG. 14 shows an exemplary embodiment of a body fluid extraction device 1400 based on the embodiment described in FIGS. 1-3. Reference numerals of structural elements of the body fluid extraction device 1400 that correspond to structural elements of the body fluid extraction devices 100, 200 and 300 of FIGS. 1, 2 and 3 differ only in their first digits, which are "15" instead of "1", "2" and "3", respectively. Therefore, for brevity of the present description, reference is also made to the description of FIGS. 1, 2 and 3 for details of these structural elements. The following description mainly concentrates on features distinguishing the device 1400 from the devices 100, 200 and 300.

The body fluid extraction device 1400 is also configured to test at least one predetermined analyte or property of the body fluid. It further comprises a solution chamber 1422 comprising a buffer solution 1424. It also comprises a collection unit 1402 that is analogous in function to the collection chamber described in reference to FIGS. 10-12. The collection unit 1402 comprises a capillary wick (not shown) configured to transport at least a fraction of the body fluid away from an input end that is located in the vicinity of an inner side 1412 of a needle carrier 1408. Further, the body fluid extraction device comprises a testing chamber 1444 that includes a testing unit 1446 having a reactive material 1448. A first transfer of the buffer solution 1424 from the solution chamber 1422 to the collection unit 1402 in a first step, and a second transfer of the buffer solution and the bodily fluid from the collection unit 1402 to the testing chamber 1444 in a second step are controlled by flow control means 1426.1 and 1426.2 respectively. In some advantageous embodiments the flow control means 1426.1 and 1426.2 comprise a first and a second cannula respectively, and the solution chamber and the testing chamber comprise a first and a second pierceable wall section respectively, as described with reference to FIG. 11. The piercing of the first and second pierceable wall sections is in these embodiments caused by the induced snap movement of a needle carrier 1408 relative to a support structure 1414.

Thus a snap dome tripper as disclosed with respect to the embodiments shown in FIGS. 1-8 is advantageously configured to operate a body fluid extraction device exhibiting pierceable wall sections.

The functionality of testing the body fluid can be also implemented as shown above in reference to FIG. 14 to any of the embodiments of the body fluid extraction device described with reference to FIGS. 1-8.

While the present invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single step or other units may fulfill the functions of several items recited in the claims.

The mere fact that certain measures are recited in mutually different dependent claims does not indicate that a combination of these measures cannot be used to advantage.

Any reference signs in the claims should not be construed as limiting the scope.

The invention claimed is:

1. A body fluid extraction device for extracting a body fluid and for testing at least one predetermined analyte or property of the body fluid, the body fluid extraction device comprising:
    at least one hollow needle having a base end and a tip and a channel linking the base end and the tip in fluid communication
    a collection chamber having an input end in fluid communication with the channel, the collection chamber comprising a capillary wick configured to transport at least a fraction of the body fluid away from the input end;
    a testing chamber comprising at least one testing unit that includes a respective reacting material configured to react in a predetermined manner to a predetermined analyte or property of the body fluid;
    a solution chamber, comprising a buffer solution;
    flow control means configured to control, in a first step, a first transfer of the buffer solution from the solution chamber to the collection chamber, and in a second step a second transfer of the body fluid and the buffer solution from the collection chamber to the testing chamber,
wherein the buffer solution is transferred to the collection chamber via the input end of the collection chamber.

2. The body fluid extraction device according to claim 1, wherein the hollow needle, the collection chamber and the solution chamber are arranged inside a sealed chamber, wherein the testing chamber is arranged outside the sealed chamber and wherein the sealed chamber and the testing chamber are configured to be brought into fluid communication upon transferring the body fluid and the buffer solution from the collection chamber to the testing chamber.

3. The body fluid extraction device according to claim 1, wherein the at least one testing unit comprises a respective lateral flow assay unit that includes:
   a sample pad configured to adsorb the body fluid and the buffer solution after the second transfer; and
   a testing capillary wick connected to the sample pad and wherein the reacting material is arranged on the testing capillary wick.

4. The body fluid extraction device according to claim 3, comprising a plurality of testing units arranged to share a common sample pad and wherein the respective testing capillary wicks extend radially from a common center formed by the common sample pad.

5. The body fluid extraction device according to claim 1, wherein the solution chamber comprises a first pierceable wall section and wherein the flow control means comprises at least one first cannula configured to pierce the first pierceable wall section, and upon piercing the first pierceable wall section to bring the solution chamber in fluid communication with the collection chamber.

6. The body fluid extraction device according to claim 5, wherein the testing chamber comprises a second pierceable wall section and wherein the flow control means comprises at least one second cannula configured to pierce the second pierceable wall section and, upon piercing the second pierceable wall section, to bring the collection chamber in fluid communication with the testing chamber.

7. The body fluid extraction device according to claim 1, wherein the testing chamber comprises a second pierceable wall section and wherein the flow control means comprises at least one second cannula configured to pierce the second pierceable wall section and, upon piercing the second pierceable wall section, to bring the collection chamber in fluid communication with the testing chamber.

8. The body fluid extraction device according to claim 1, wherein the flow control means comprise a first fluid connection between the solution chamber and the collection chamber, the first fluid connection being controllable by a first valve in dependence on a predetermined first control signal, and a second fluid connection between the collection chamber and the testing chamber, the second fluid connection being controllable by a second valve in dependence on a predetermined second control signal.

9. The body fluid extraction device according to claim 1, wherein an inner wall of the channel of the hollow needle is at least partially covered by a covering layer comprising a hydrophilic material.

10. A body fluid extraction device for extracting a body fluid and for testing at least one predetermined analyte or property of the body fluid, the body fluid extraction device comprising:
    at least one hollow needle having a base end and a tip and a channel linking the base end and the tip in fluid communication
    a collection chamber having an input end in fluid communication with the channel, the collection chamber comprising a capillary wick configured to transport at least a fraction of the body fluid away from the input end;
    a testing chamber comprising at least one testing unit that includes a respective reacting material configured to react in a predetermined manner to a predetermined analyte or property of the body fluid;
    a solution chamber, comprising a buffer solution;
    flow control means configured to control, in a first step, a first transfer of the buffer solution from the solution chamber to the collection chamber, and in a second step a second transfer of the body fluid and the buffer solution from the collection chamber to the testing chamber,
    wherein the hollow needle, the collection chamber and the solution chamber are arranged inside a sealed chamber, wherein the testing chamber is arranged outside the sealed chamber and wherein the sealed chamber and the testing chamber are configured to be brought into fluid communication upon transferring the body fluid and the buffer solution from the collection chamber to the testing chamber.

11. The body fluid extraction device according to claim 10, wherein the at least one testing unit comprises a respective lateral flow assay unit that includes:
    a sample pad configured to adsorb the body fluid and the buffer solution after the second transfer; and
    a testing capillary wick connected to the sample pad and wherein the reacting material is arranged on the testing capillary wick.

12. The body fluid extraction device according to claim 11, comprising a plurality of testing units arranged to share a common sample pad and wherein the respective testing capillary wicks extend radially from a common center formed by the common sample pad.

13. The body fluid extraction device according to claim 10, wherein the solution chamber comprises a first pierceable wall section and wherein the flow control means comprises at least one first cannula configured to pierce the first pierceable wall section, and upon piercing the first pierceable wall section to bring the solution chamber in fluid communication with the collection chamber.

14. The body fluid extraction device according to claim 10, wherein the testing chamber comprises a second pierceable wall section and wherein the flow control means comprises at least one second cannula configured to pierce the second pierceable wall section and, upon piercing the second pierceable wall section, to bring the collection chamber in fluid communication with the testing chamber.

15. The body fluid extraction device according to claim 10, wherein the flow control means comprise a first fluid connection between the solution chamber and the collection chamber, the first fluid connection being controllable by a first valve in dependence on a predetermined first control signal, and a second fluid connection between the collection chamber and the testing chamber, the second fluid connection being controllable by a second valve in dependence on a predetermined second control signal.

16. The body fluid extraction device according to claim 15, wherein the testing chamber comprises a second pierceable wall section and wherein the flow control means comprises at least one second cannula configured to pierce the second pierceable wall section and, upon piercing the second pierceable wall section, to bring the collection chamber in fluid communication with the testing chamber.

17. The body fluid extraction device according to claim 10, wherein an inner wall of the channel of the hollow needle is at least partially covered by a covering layer comprising a hydrophilic material.

18. A body fluid extraction device for extracting a body fluid and for testing at least one predetermined analyte or property of the body fluid, the body fluid extraction device comprising:
    at least one hollow needle having a base end and a tip and a channel linking the base end and the tip in fluid communication a collection chamber having an input end in fluid communication with the channel, the collection chamber comprising a capillary wick configured to transport at least a fraction of the body fluid away from the input end;

a testing chamber comprising at least one testing unit that includes a respective reacting material configured to react in a predetermined manner to a predetermined analyte or property of the body fluid;

a solution chamber, comprising a buffer solution;

flow control means configured to control, in a first step, a first transfer of the buffer solution from the solution chamber to the collection chamber, and in a second step a second transfer of the body fluid and the buffer solution from the collection chamber to the testing chamber, wherein the testing chamber comprises a pierceable wall section and wherein the flow control means comprises at least one cannula configured to pierce the pierceable wall section and, upon piercing the pierceable wall section, to bring the collection chamber in fluid communication with the testing chamber.

19. The body fluid extraction device according to claim 18, wherein the at least one testing unit comprises a respective lateral flow assay unit that includes:

a sample pad configured to adsorb the body fluid and the buffer solution after the second transfer; and a testing capillary wick connected to the sample pad and wherein the reacting material is arranged on the testing capillary wick.

20. The body fluid extraction device according to claim 19, comprising a plurality of testing units arranged to share a common sample pad and wherein the respective testing capillary wicks extend radially from a common center formed by the common sample pad.

21. The body fluid extraction device according to claim 18, wherein the solution chamber comprises a further pierceable wall section and wherein the flow control means comprises at least one further cannula configured to pierce the further pierceable wall section, and upon piercing the further pierceable wall section to bring the solution chamber in fluid communication with the collection chamber.

22. The body fluid extraction device according to claim 18, wherein the flow control means comprise a first fluid connection between the solution chamber and the collection chamber, the first fluid connection being controllable by a first valve in dependence on a predetermined first control signal, and a second fluid connection between the collection chamber and the testing chamber, the second fluid connection being controllable by a second valve in dependence on a predetermined second control signal.

23. The body fluid extraction device according to claim 18, wherein an inner wall of the channel of the hollow needle is at least partially covered by a covering layer comprising a hydrophilic material.

* * * * *